(12) United States Patent
Kravtchenko et al.

(10) Patent No.: US 8,097,046 B2
(45) Date of Patent: Jan. 17, 2012

(54) DYE COMPOSITION COMPRISING AT LEAST ONE INSOLUBLE COMPOUND AND PROCESSES USING THIS COMPOSITION

(75) Inventors: Sylvain Kravtchenko, Shanghai (CN); Claude Dubief, Le Chesnay (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 13/024,029

(22) Filed: Feb. 9, 2011

(65) Prior Publication Data

US 2011/0126362 A1 Jun. 2, 2011

Related U.S. Application Data

(62) Division of application No. 11/509,023, filed on Aug. 24, 2006, now Pat. No. 7,905,925.

(60) Provisional application No. 60/785,987, filed on Mar. 27, 2006.

(30) Foreign Application Priority Data

Aug. 25, 2005  (FR) ...................................... 05 08753

(51) Int. Cl.
*A61Q 5/10* (2006.01)

(52) U.S. Cl. ............. 8/405; 8/406; 8/408; 8/410; 8/412; 8/435; 8/512; 8/552

(58) Field of Classification Search ............... 8/405, 406, 8/408, 410, 412, 435, 512, 552
See application file for complete search history.

(56) References Cited

U.S. PATENT DOCUMENTS

2005/0015896 A1* 1/2005 Pratt et al. ...................... 8/405
* cited by examiner

*Primary Examiner* — Eisa Elhilo

(74) *Attorney, Agent, or Firm* — Finnegan, Henderson, Farabow, Garrett & Dunner, LLP

(57) ABSTRACT

Disclosed herein is an aqueous dye composition for dyeing keratin fibers, for example, human keratin fibers such as the hair, comprising, in a suitable dyeing medium: (a) at least one oxidizing agent, (b) at least one water-insoluble oxygenated organic non-dyeing compound, present in an amount of at least 30% by weight relative to the total weight of the dye composition, and (c) at least one oxidation dye precursor and/or at least one direct dye. Also disclosed herein is a process for dyeing human keratin fibers, for example, the hair, comprising applying such a composition to the keratin fibers.

28 Claims, No Drawings

DYE COMPOSITION COMPRISING AT LEAST ONE INSOLUBLE COMPOUND AND PROCESSES USING THIS COMPOSITION

This is a division of Application Ser. No. 11/509,023, filed Aug. 24, 2006 now U.S. Pat. No. 7,905,925, which claims benefit of U.S. Provisional Application No. 60/785,987, filed Mar. 27, 2006, the contents of all of which are incorporated herein by reference. This application also claims benefit of priority under 35 U.S.C. §119 to French Patent Application No. FR 05 08753, filed Aug. 23, 2005, the contents of which are also incorporated herein by reference.

Disclosed herein are compositions for dyeing keratin materials, comprising at least one water-insoluble compound. Also disclosed herein is a process for dyeing human keratin fibers, for example, the hair, comprising applying such a composition to the keratin fibers.

It is known practice to dye keratin fibers, for example, human hair, with dye compositions comprising oxidation dye precursors, which are generally known as oxidation bases. These oxidation bases are colorless or weakly colored compounds, which, when combined with oxidizing products, give rise to colored compounds by a process of oxidative condensation.

It is also known that the shades obtained with these oxidation bases may be varied by combining them with couplers or coloration modifiers. The variety of molecules available as oxidation bases and couplers allows a rich palette of colors to be obtained.

This process of oxidation dyeing comprises applying to the keratin fibers at least one oxidation base or a mixture of at least one oxidation base and at least one coupler, with an oxidizing agent, for example, aqueous hydrogen peroxide solutions, leaving the mixture to act on the fibers, and then rinsing the fibers. The colorations resulting therefrom may be permanent, strong, and resistant to external agents, for example, light, bad weather, washing, perspiration, and/or rubbing. This process, which is generally performed at basic pH, may allow dyeing and simultaneous lightening of the fiber to be obtained, which is reflected in practice by the possibility of obtaining a final coloration that is lighter than the original color. In addition, lightening of the fibers may have the advantageous effect of generating a unified color in the case of grey hair, and, in the case of naturally pigmented hair, of bringing out the color, i.e., making it more visible.

It is also known practice to dye keratin fibers by direct dyeing. The process conventionally used in direct dyeing comprises applying to the keratin fibers at least one direct dye, which may be chosen from colored and coloring molecules that have affinity for the fibers, leaving the at least one dye to act and then rinsing the fibers.

It is known practice, for example, to use nitrobenzene dyes, anthraquinone dyes, nitropyridine dyes, azo dyes, xanthene dyes, acridine dyes, azine dyes, and triarylmethane dyes as direct dyes.

The colorations resulting therefrom are colorations that may be particularly chromatic, but which are, however, temporary or semi-permanent. The nature of the interactions that bind the direct dyes to the keratin fiber, and their desorption from the surface and/or from the core of the fiber, are such that the dyeing power and the wash-fastness or perspiration-fastness of the colorations may still be considered insufficient. These direct dyes may also be light-sensitive due to the low resistance of the chromophore to photochemical attack, and may lead to fading of the coloration of the hair over time. In addition, their light sensitivity is dependent on their uniform distribution or distribution as aggregates in the keratin fiber.

It is known practice to use direct dyes in combination with oxidizing agents. However, direct dyes may be sensitive to the action of oxidizing agents such as aqueous hydrogen peroxide solution, and reducing agents such as sodium bisulfite, which may make them difficult to use in lightening direct dye compositions based on hydrogen peroxide and a basifying agent or in oxidation dye compositions in combination with precursors such as oxidation bases or couplers. It has been proposed, for example, in Japanese Patent Applications 53 95693 and 55 022 638, to dye the hair with compositions based on cationic direct dyes of oxazine type and ammoniacal hydrogen peroxide solution, by applying ammoniacal hydrogen peroxide solution to the hair in a first step, followed by a composition based on the oxazine direct dye in a second step. However, this coloration is unsatisfactory because the dyeing process is made too slow by the leave-on times of the two successive steps. Moreover, if an extemporaneous mixture of the oxazine direct dye with ammoniacal hydrogen peroxide solution is applied to the hair, no dyeing is produced or, at the very best, a virtually nonexistent coloration of the hair fiber is obtained.

The leave-on time of a lightening direct dye or oxidation dye composition conventionally ranges from 15 to 45 minutes, depending on the nature of the fiber (sensitized or non-sensitized) and the nature of the dye used. A great deal of research has been conducted on reducing the leave-on time of dye compositions without, however, increasing the concentration of the constituents, while at the same time maintaining a good level of dyeing, i.e., good dyeing power and good fastness of the color with respect to external agents and over time.

Thus, it would be useful to provide lightening direct dye or oxidation dye compositions that are improved in terms of efficacy and speed of reaction and/or of penetration of the dye into the fiber, while at the same time maintaining good harmlessness, good resistance, and good selectivity, the latter resulting from the difference in color uptake between different parts of a hair or of a head of hair.

The present inventors have discovered that the use of a composition comprising at least one dyeing agent chosen from oxidation dye precursors and direct dyes, at least one oxidizing agent, and at least one water-insoluble oxygenated organic compound for dyeing keratin fibers, for example, human keratin fibers such as the hair, may provide at least one of the improvements mentioned above.

These compositions may have the advantage of harmlessness, may allow a shorter application of the composition to the fibers to be dyed, and thus shorter contact with the oxidizing agents, which have a tendency to deteriorate the fiber, and may allow uniform, resistant tints to be obtained.

In addition, these compositions may have a good toxicological profile.

Also disclosed herein are processes for the oxidation dyeing and/or lightening dyeing of keratin fibers comprising applying at least one composition of the present disclosure to the fibers.

Other characteristics, aspects, subjects and advantages of the invention will be understood more clearly upon reading the description below.

Disclosed herein is an aqueous dye composition for dyeing keratin fibers, for example, human keratin fibers such as the hair, comprising, in a suitable dyeing medium:
(a) at least one oxidizing agent,
(b) at least one water-insoluble oxygenated organic non-dyeing compound, present in an amount of at least 30% by weight relative to the total weight of the dye composition, and (c) at least one oxidation dye precursor and/or at least one direct dye.

The at least one oxidizing agent may be chosen from hydrogen peroxide and compounds capable of producing hydrogen peroxide by hydrolysis, such as urea peroxide, alkali metal bromates, persalts such as perborates, persulfates, percarbonates, and peroxides of alkali metals and alkaline-earth metals, for instance, of sodium, potassium, and magnesium, and peracids, and mixtures thereof; and oxidase enzymes, for example, peroxidases, 2-electron oxidoreductases such as uricases and 4-electron oxygenases, for instance, laccases, where appropriate in the presence of the appropriate substrate thereof. In at least one embodiment, the at least one oxidizing agent is hydrogen peroxide.

The at least one oxidizing agent may be present in the dye composition in an amount ranging from 2% to 35% by weight, for example, from 5% to 30% by weight, relative to the total weight of the dye composition.

As used herein, the term "oxygenated organic compound" means any organic compound comprising at least one oxygen atom in its elemental molecular structure.

As used herein, the term "water-insoluble oxygenated organic no-dyeing compound" means oxygenated compounds with a solubility in water at room temperature (25° C.) of less than 0.5% by weight. The oxygenated organic compounds of the present disclosure may be polymeric or non-polymeric compounds.

The polymeric insoluble oxygenated organic compounds according to the present disclosure may be chosen, for example, from polyamides 6, 66, and 11, polyesters, polyurethanes, polycyanoacrylates, polymethyl methacrylates, polycarbonates, Teflon® (polytetrafluoroethylene), and silicone resins and elastomers.

The non-polymeric oxygenated organic compounds of the present disclosure may be chosen, for example, from fatty alcohols, fatty acid esters, amides, and ethers, and fatty alcohol esters, amides, and ethers. Examples of fatty acid and fatty alcohol esters, amides, and ethers include, but are not limited to, those having fatty chains of fatty acids or fatty alcohols comprising from 8 to 40 carbon atoms, which are optionally hydroxylated. Suitable fatty alcohols may include, for example, fatty alcohols comprising from 8 to 40 carbon atoms, such as ethylene glycol monostearate; ethylene glycol distearate; pentaerythrityl monooleate; sorbitan tristearate; glyceryl dioleate; fatty esters, amides, and ethers of ethylene glycol; fatty esters, amides, and ethers of propylene glycol, distearyl ether; stearyl alcohol; behenyl alcohol; and cetyl-stearyl alcohol.

The at least one water-insoluble oxygenated organic non-dyeing compound may be present in the composition in an amount of greater than 30% by weight relative to the total weight of the dye composition, for example, from 30% to 75% by weight, or from 30% and 60% by weight.

Thus, in at least one embodiment, when the at least one water-insoluble compound according to the present disclosure is solid, the composition is in the form of a suspension. In another embodiment, when the at least one water-insoluble compound according to the present disclosure is in liquid form, for example, in the form of an organic phase that is insoluble in the aqueous phase, the composition is in a form chosen from emulsions and dispersions.

The composition of the present disclosure may also comprise at least one oxidation dye precursor.

The at least one oxidation dye precursor may be chosen, for example, from phenylenediamines, bis(phenyl)alkylenediamines, para-aminophenols, ortho-aminophenols, heterocyclic bases, and the addition salts thereof.

Examples of para-phenylenediamines include, but are not limited to, para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylene-diamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N -(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine, and the acid addition salts thereof.

In at least one embodiment, the para-phenylenediamines may be chosen, for example, from para-phenylenediamine, para-tolylenediamine, 2-isopropyl-para-phenyl-enediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and the acid addition salts thereof.

Suitable bis(phenyl)alkylenediamines include, for example, N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methyl-phenyl) ethylenediamine, 1,8-bis(2,5-diaminophenoxy)-3,6-dioxaoctane, and the addition salts thereof.

Non-limiting examples of para-aminophenols include para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylamino-methyl)phenol, 4-amino-2-fluorophenol, and the acid addition salts thereof.

Ortho-aminophenols may be chosen, for example, from 2-aminophenol, 2-amino-5-methylphenol, 2-amino-6-methylphenol, 5-acetamido-2-aminophenol, and the addition salts thereof.

Suitable heterocyclic bases may include, for example, pyridine derivatives, pyrimidine derivatives, and pyrazole derivatives.

Examples of pyridine derivatives include, but are not limited to, the compounds described, for example, in British Patent Nos. 1 026 978 and 1 153 196, as well as 2,5-diaminopyridine, 2-(4-methoxyphenyl)amino-3-aminopyridine, 3,4-diaminopyridine, and the addition salts thereof.

Other examples of pyridine oxidation bases that are useful in accordance with the present disclosure include the 3-aminopyrazolo[1,5-a]pyridine oxidation bases and addition salts thereof described, for example, in French Patent Application No. 2 801 308, for instance, pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamino, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-yl-pyrazolo[1,5-a]pyrid-3-ylamine, 2-[(3-aminopyrazolo[1,5-a]pyrid-5-yl)(2-hydroxy-ethyl)amino]ethanol, 2-[(3-aminopyrazolo[1,5-a]pyrid-7-yl)(2-hydroxy-ethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, and the addition salts thereof.

Non-limiting examples of pyrimidine derivatives include the compounds described, for example, in patents German Patent No. 2 359 399; Japanese Patent Application No. 88-169 571 (published as JP 02-19576); Japanese Patent No. 05-163124; European Patent Application No. 0 770 375, and International Patent Application Publication No. WO 96/15765, for instance 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, the addition salts thereof, and the tautomeric forms thereof, when a tautomeric equilibrium exists.

Suitable pyrazole derivatives include, but are not limited to, the compounds described in German Patent Nos. 3 843 892 and 4 133 957, International Patent Application Nos. WO 94/08969 and WO 94/08970, French Patent Application No. 2 733 749, and German Patent Application No. 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof. In at least one embodiment, 4,5-diamino-1-(β-methoxyethyl)pyrazole may be used as a suitable pyrazole derivative.

The at least one oxidation dye precursor may be present in the dye composition of the present disclosure in an amount ranging from 0.001% to 20% by weight, for example, from 0.005% to 6% by weight, relative to the total weight of the dye composition.

The dye composition in accordance with the present disclosure may also comprise at least one direct dye chosen from neutral, acidic, or cationic nitrobenzene dyes; neutral, acidic, or cationic azo direct dyes; neutral, acidic, or cationic quinone, for example, anthraquinone, direct dyes; azine direct dyes; triarylmethane direct dyes; indoamine direct dyes; and natural direct dyes.

Examples of benzene-based direct dyes that may be used in accordance with the present disclosure include, for example:
1,4-diamino-2-nitrobenzene,
1-amino-2-nitro-4-β-hydroxyethylaminobenzene,
1-amino-2-nitro-4-bis(β-hydroxyethyl)aminobenzene,
1,4-bis(β-hydroxyethylamino)-2-nitrobenzene,
1-β-hydroxyethylamino-2-nitro-4-bis(β-hydroxyethylamino)benzene,
1-β-hydroxyethylamino-2-nitro-4-aminobenzene,
1-β-hydroxyethylamino-2-nitro-4-(ethyl)(β-hydroxyethyl)aminobenzene,
1-amino-3-methyl-4-β-hydroxyethylamino-6-nitrobenzene,
1-amino-2-nitro-4-β-hydroxyethylamino-5-chlorobenzene,
1,2-diamino-4-nitrobenzene,
1-amino-2-β-hydroxyethylamino-5-nitrobenzene,
1,2-bis(β-hydroxyethylamino)-4-nitrobenzene,
1-amino-2-tris(hydroxymethyl)methylamino-5-nitrobenzene,
1-hydroxy-2-amino-5-nitrobenzene,
1-hydroxy-2-amino-4-nitrobenzene,
1-hydroxy-3-nitro-4-aminobenzene,
1-hydroxy-2-amino-4,6-dinitrobenzene,
1-β-hydroxyethyloxy-2-β-hydroxyethylamino-5-nitrobenzene,
1-methoxy-2-β-hydroxyethylamino-5-nitrobenzene,
1-β-hydroxyethyloxy-3-methylamino-4-nitrobenzene,
1-β,γ-dihydroxypropyloxy-3-methylamino-4-nitrobenzene,
1-β-hydroxyethylamino-4-β,γ-dihydroxypropyloxy-2-nitrobenzene,
1-β,γ-dihydroxypropylamino-4-trifluoromethyl-2-nitrobenzene,
1-β-hydroxyethylamino-4-trifluoromethyl-2-nitrobenzene,
1-β-hydroxyethylamino-3-methyl-2-nitrobenzene,
1-β-aminoethylamino-5-methoxy-2-nitrobenzene,
1-hydroxy-2-chloro-6-ethylamino-4-nitrobenzene,
1-hydroxy-2-chloro-6-amino-4-nitrobenzene,
1-hydroxy-6-bis(β-hydroxyethyl)amino-3-nitrobenzene,
1-β-hydroxyethylamino-2-nitrobenzene, and
1-hydroxy-4-β-hydroxyethylamino-3-nitrobenzene.

Suitable azo direct dyes include, for example, the cationic azo dyes described in International Patent Application Publication Nos. WO 95/15144, WO 95/01772, WO 02/078 660; WO 02/100 834, and WO 02/100 369, European Patent Application No. 0 714 954, and French Patent Application Nos. 2 822 696, 2 825 702, 2 825 625, 2 822 698, 2 822 693, 2 822 694, 2 829 926, 2 807 650, and 2 844 269, which are incorporated herein by reference in their entireties.

These azo compounds may include, for example:
1,3-dimethyl-2[[4-(dimethylamino)phenyl]azo]-1H-imidazolium chloride,
1,3-dimethyl-2-[(4-aminophenyl)azo]-1H-imidazolium chloride, and
1-methyl-4-[(methylphenylhydrazono)methyl]pyridinium methyl sulfate.

Other examples of azo direct dyes include, but are not limited to, the following dyes, described in the Color Index International, 3rd edition:

Disperse Red 17,
Acid Yellow 9,
Acid Black 1,
Basic Red 22,
Basic Red 76,
Basic Yellow 57,
Basic Brown 16,
Acid Yellow 36,
Acid Orange 7,
Acid Red 33,
Acid Red 35,
Basic Brown 17,
Acid Yellow 23,
Acid Orange 24, and
Disperse Black 9.

1-(4'-aminodiphenylazo)-2-methyl-4-bis(β-hydroxyethyl)aminobenzene and 4-hydroxy-3-(2-methoxyphenylazo)-1-naphthalenesulfonic acid may also be used as suitable azo direct dyes.

Non-limiting examples of quinone direct dyes include:
Disperse Red 15,
Solvent Violet 13,
Acid Violet 43,
Disperse Violet 1,
Disperse Violet 4,
Disperse Blue 1,
Disperse Violet 8,
Disperse Blue 3,
Disperse Red 11,
Acid Blue 62,
Disperse Blue 7,
Basic Blue 22,
Disperse Violet 15,
Basic Blue 99,
1-N-methylmorpholiniumpropylamino-4-hydroxyanthraquinone,
1-aminopropylamino-4-methylaminoanthraquinone,
1-aminopropylaminoanthraquinone,
5-β-hydroxyethyl-1,4-diaminoanthraquinone,
2-aminoethylaminoanthraquinone, and
1,4-bis(β,γ-dihydroxypropylamino)anthraquinone.

Suitable azine dyes may include, for example:
Basic Blue 17, and
Basic Red 2.

Triarylmethane dyes may be chosen, for example, from:
Basic Green 1,
Acid blue 9,
Basic Violet 3,
Basic Violet 14,
Basic Blue 7,
Acid Violet 49,
Basic Blue 26, and
Acid Blue 7.

Examples of indoamine dyes include, but are not limited to:
2-β-hydroxyethylamino-5-[bis(β-4'-hydroxyethyl)amino]anilino-1,4-benzoquinone,
2-β-hydroxyethylamino-5-(2'-methoxy-4'-amino)anilino-1,4-benzoquinone,
3-N-(2'-chloro-4'-hydroxy)phenylacetylamino-6-methoxy-1,4-benzoquinone imine,
3-N-(3'-chloro-4'-methylamino)phenylureido-6-methyl-1,4-benzoquinone imine, and
3-[4'-N-(ethyl,carbamylmethyl)amino]phenylureido-6-methyl-1,4-benzoquinone imine.

Non-limiting examples of natural direct dyes include lawsone, juglone, alizarin, purpurin, carminic acid, kermesic acid, purpurogallin, protocatechaldehyde, indigo, isatin, curcumin, spinulosin, and apigenidin. It is also possible to use extracts and decoctions containing these natural dyes, for example, henna-based poultices and extracts.

The at least one direct dye may be present in the dye composition in an amount ranging from 0.001% to 20% by weight relative to the total weight of the dye composition, for example, from 0.005% to 10% by weight.

In at least one embodiment, if the dye composition comprises at least one oxidation dye precursor, the composition also comprises at least one coupler conventionally used for dyeing keratin fibers. Examples of suitable couplers include, but are not limited to, meta-phenylenediamines, meta-aminophenols, meta-diphenols, naphthalene-based couplers, and heterocyclic couplers, and the addition salts thereof.

Additional examples of couplers include 1,3-dihydroxybenzene, 1,3-dihydroxy-2-methylbenzene, 4-chloro-1,3-dihydroxybenzene, 2,4-diamino-1-(β-hydroxyethyloxy)-benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxy-pyridine, 6-hydroxybenzomorpholine, 3,5-diamino-2,6-dimethoxypyridine, 1-N-(β-hydroxy-ethyl)amino-3,4-methylenedioxybenzene, 2,6-bis(β-hydroxyethylamino)toluene, and the addition salts thereof.

The at least one coupler may be present in the dye composition in an amount ranging from 0.001% to 20%, for example, from 0.005% to 6% by weight relative to the total weight of the dye composition.

The addition salts of the oxidation bases and couplers that may be used in the context of the invention may be chosen, for example, from acid addition salts, such as hydrochlorides, hydrobromides, sulfates, citrates, succinates, tartrates, lactates, tosylates, benzenesulfonates, phosphates, and acetates, and base addition salts, such as sodium hydroxide, potassium hydroxide, ammonia, amines, and alkanolamines.

The suitable dyeing medium, also known as the dye support, is a cosmetic medium chosen from water and mixtures of water and at least one organic solvent. Examples of suitable organic solvents include, but are not limited to, $C_1$-C4 lower alkanols, such as ethanol and isopropanol; polyols and polyol ethers, for instance 2-butoxyethanol, propylene glycol, glycerol, polyol monoethers such as propylene glycol monomethyl ether, diethylene glycol monoethyl ether, and monomethyl ether, and aromatic alcohols, for instance, benzyl alcohol and phenoxyethanol; and mixtures thereof.

The dye composition according to the present disclosure may comprise water, present in an amount ranging from 0.1% to 69%, for example, from 10% to 68%, from 20% to 65%, or from 30% to 60% by weight relative to the total weight of the dye composition.

The at least one organic solvent may be present in the composition in an amount ranging from 1% to 40% by weight, for example, from 5% to 30% by weight relative to the total weight of the dye composition.

The dye composition in accordance with the present disclosure may also comprise at least one adjuvant conventionally used in hair dye compositions, such as anionic, cationic, nonionic, amphoteric, or zwitterionic surfactants and mixtures thereof; anionic, cationic, nonionic, amphoteric, or zwitterionic polymers and mixtures thereof, different from those disclosed above; mineral and organic thickeners, for example, anionic, cationic, nonionic, and amphoteric associative thickeners; antioxidants; penetrants; sequestrants; fragrances; buffers; dispersants; conditioning agents, for instance, volatile or non-volatile, modified or unmodified silicones; film-forming agents; ceramides; preserving agents; and opacifiers.

The at least one adjuvant may be present in the composition in an amount, for each of them, ranging from 0.01% to 20% by weight relative to the total weight of the composition.

It is to be understood that a person skilled in the art will take care to select the at least one optional additional compound such that the advantageous properties intrinsically associated with the dye composition in accordance with the present disclosure are not, or are not substantially, adversely affected by the envisaged addition.

The pH of the dye composition in accordance with the present disclosure may range from 3 to 12, for example, from 5 to 11, or from 6 to 8.5. The pH may be adjusted to the desired value by means of acidifying or basifying agents conventionally used for dyeing keratin fibers, or alternatively, using standard buffer systems.

Examples of acidifying agents include, but are not limited to, mineral and organic acids such as hydrochloric acid, orthophosphoric acid, sulfuric acid, carboxylic acids, for instance acetic acid, tartaric acid, citric acid, and lactic acid, and sulfonic acids.

Non-limiting examples of basifying agents include aqueous ammonia, alkaline carbonates, alkanolamines such as monoethanolamine, diethanolamine, and triethanolamine, and derivatives thereof, sodium hydroxide, potassium hydroxide, and compounds of formula (II):

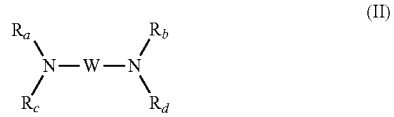

(II)

wherein:
W is chosen from propylene residues optionally substituted with at least one entity chosen from hydroxyl groups and $C_1$-$C_4$ alkyl radicals; and
$R_a$, $R_b$, $R_c$, and $R_d$, which may be identical or different, are chosen from hydrogen, $C_1$-$C_4$ alkyl radicals, and $C_1$-$C_4$ hydroxyalkyl radicals.

In at least one embodiment, the composition may result from the extemporaneous mixing of two or more compositions. For example, the composition may be obtained by mixing a composition comprising the at least one oxidizing agent and a composition comprising the at least one water-insoluble oxygenated non-dyeing organic compound and the at least one dye.

The dye composition according to the present disclosure may be in various forms, such as liquids, creams, and gels, or in any other form that is suitable for dyeing keratin fibers, for example, human hair. This is likewise the case for the compositions which, after mixing together, lead to the composition according to the invention, with the proviso that one of the compositions is in the form of an aqueous solution.

Also disclosed herein is a process for dyeing keratin fibers comprising applying a composition of the present disclosure to the fibers, and rinsing the fibers.

In at least one embodiment, the process may comprise applying the dye composition to the keratin fibers, leaving it to act for a time period ranging from 3 minutes and 1 hour, such as from 15 minutes to 45 minutes, and the said fibers are then rinsed.

Thus, when the composition according to the present disclosure used in the dyeing process comprises, as dye, at least one oxidation dye precursor, optionally combined with at least one coupler, the process according to the present disclosure is an oxidation dyeing process.

When the composition according to the present disclosure used in the dyeing process does not comprise any oxidation dye precursors, and comprises at least one direct dye, the process according to the present disclosure is a lightening direct dyeing process.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the present disclosure are approximations, unless otherwise indicated the numerical values set forth in the specific examples are reported as precisely as possible. Any numerical value, however, inherently contain certain errors necessarily resulting from the standard deviation found in their respective testing measurements.

By way of non-limiting illustration, concrete examples of certain embodiments of the present disclosure are given below.

EXAMPLES

The following ready-to-use dye compositions were prepared:

| | |
|---|---|
| Dye** | x g |
| Distearyl ether | 32 g |
| Sodium lauryl sulphate | 1.5 g |
| Brij 700 | 1 g |
| Ammonium acryloyldimethyltaurate/Steareth 25 crosspolymer sodium stannate hexahydrate | 0.02 g |
| EDTA | 0.01 g |
| Tetrasodium pyrophosphate decahydrate | 0.015 g |
| Hydrogen peroxide | 3 g |
| Phosphoric acid | 0.015 g |
| Aqueous ammonia containing 20% $NH_3$ | 5.0 g |
| Demineralized water | qs 100 g |

**The dye was chosen as follows for Examples 1 and 2:

| | | |
|---|---|---|
| Example 1 | Para-Phenylenediamine | 0.162 g |
| | 2-Methyl-5-aminophenol | 0.1845 g |
| Example 2 | Basic Orange 51 | 0.1 g |

The compositions of Example 1 or 2 were applied, immediately after preparation, to chestnut-brown hair. After a leave-on time of 30 minutes, the hair was rinsed and dried. It had luminous shades with a mahogany tint in Example 1 and a coppery tint in Example 2. The lightening of the natural base was substantial.

Similar results may be obtained by replacing the distearyl ether weight-for-by weight with Nylon-6 powder sold by Induchem under the name INDUCOS.

What is claimed is:

1. An aqueous dye composition for dyeing keratin fibers comprising, in a suitable dyeing medium:
   (a) at least one oxidizing agent,
   (b) at least 30% by weight of at least one water-insoluble oxygenated organic no-dyeing compound of polymeric nature relative to the total weight of the said composition, and
   (c) at least one oxidation dye precursor or one direct dye.

2. A composition according to claim 1, characterized in that the keratin fibers are human hair.

3. A composition according to claim 1, characterized in that the oxidizing agent is chosen from hydrogen peroxide, urea peroxide, alkali metal bromates, alkali metal or alkaline-earth metal perborates, persulfates, percarbonates or peroxides, and peracids, or mixtures thereof; and oxidase enzymes.

4. A composition according to claim 3, characterized in that the oxidizing agent is hydrogen peroxide.

5. A composition according to claim 1, characterized in that the content of the at least one oxidizing agent is between 2% and 35% by weight of the dye composition.

6. A composition according to claim 5, characterized in that the content of the at least one oxidizing agent is between 5% and 30% by weight of the dye composition.

7. A composition according to claim 1, characterized in that the water-insoluble polymeric oxygenated compounds are chosen from polyamides 6, 66 and 11, polyesters, polyurethanes, polycyanoacrylates, polymethyl methacrylates, polycarbonates, Teflon, and silicone resins or elastomers.

8. A composition according to claim 1, characterized in that the content of water-insoluble oxygenated organic compound is greater than 30% by weight of the dye composition.

9. A composition according to claim 8, characterized in that the content of water-insoluble oxygenated organic compound is between 30% and 90% by weight of the dye composition.

10. A composition according to claim 8, characterized in that the content of water-insoluble oxygenated organic compound is between 30% and 60% by weight of the dye composition.

11. A composition according to claim 1, characterized in that the oxidation dye precursor is chosen from para-phenylenediamines, bis(phenyl)alkylenediamines, para-aminophenols, ortho-aminophenols and heterocyclic bases, and the addition salts thereof.

12. A composition according to claim 11, characterized in that the oxidation dye precursor(s) is (are) present in an amount of between 0.001% and 20% by weight relative to the total weight of the composition.

13. A composition according to claim 12, characterized in that the oxidation dye precursor(s) is (are) present in an amount of between 0.005% and 6% by weight relative to the total weight of the composition.

14. A composition according to claim 1, characterized in that the direct dye is chosen from neutral, acidic or cationic nitrobenzene dyes, neutral, acidic or cationic azo direct dyes, neutral, acidic or cationic quinone and in particular anthraquinone direct dyes, azine direct dyes, triarylmethane direct dyes, indoamine direct dyes and natural direct dyes.

15. A composition according to claim 14, characterized in that the direct dye(s) is (are) present in an amount of between 0.001% and 20% by weight relative to the total weight of the composition.

16. A composition according to claim 15, characterized in that the direct dye(s) is (are) present in an amount of between 0.005% and 10% by weight relative to the total weight of the composition.

17. A composition according to claim 1, characterized in that it also comprises a coupler chosen from meta-phenylenediamines, meta-aminophenols, meta-diphenols, naphthalene-based couplers and heterocyclic couplers, and the addition salts thereof.

18. A composition according to claim 17, characterized in that the coupler is chosen from 1,3-dihydroxybenzene, 1,3-dihydroxy-2-methylbenzene, 4-chloro-1,3-dihydroxybenzene, 2,4-diamino-1-($\beta$-hydroxyethyloxy)benzene, 2-amino-4-($\beta$-hydroxyethylamino)-1-methoxybenzene, 1,3-diaminobenzene, 1,3-bis(2,4-diamino-phenoxy)propane, 3-ureidoaniline, 3-ureido-1-dimethylaminobenzene, sesamol, 1-$\beta$-hydroxyethylamino-3,4-methylenedioxybenzene, $\alpha$-naphthol, 2-methyl-1-naphthol, 6-hydroxyindole, 4-hydroxyindole, 4-hydroxy-N-methylindole, 2-amino-3-hydroxy-pyridine, 6-hydroxybenzomorpholine, 3,5-diamino-2,6-dimethoxypyridine, 1-N-($\beta$-hydroxyethyl)amino-3,4-methylenedioxybenzene and 2,6-bis($\beta$-hydroxyethyl-amino) toluene, and the addition salts thereof.

19. A composition according to claim 17, characterized in that the coupler(s) is (are) present in an amount of between 0.001% and 20% by weight relative to the total weight of the composition.

20. A composition according to claim 19, characterized in that the coupler(s) is (are) present in an amount of between 0.005% and 6% by weight relative to the total weight of the composition.

21. A composition according to claim 1, characterized in that the composition comprises at least one organic solvent such as ethanol, propylene glycol, glycerol, or polyol monoethers.

22. A composition according to claim 1, characterized in that the composition contains 0.1% to 69%, by weight of water relative to the total weight of the composition.

23. A composition according to claim 22, characterized in that the composition contains 10% to 68% by weight of water relative to the total weight of the composition.

24. A composition according to claim 23, characterized in that the composition contains 20% to 65% by weight of water relative to the total weight of the composition.

25. A composition according to claim 23, characterized in that the composition contains 30% to 60% by weight of water relative to the total weight of the composition.

26. A composition according to claim 1, characterized in that it comprises at least one adjuvant chosen from anionic, cationic, nonionic, amphoteric or zwitterionic surfactants or mixtures thereof, anionic, cationic, nonionic, amphoteric or zwitterionic polymers or mixtures thereof different from those defined above, mineral or organic thickeners, and in particular anionic, cationic, nonionic and amphoteric polymeric associative thickeners, antioxidants, penetrants, sequestrants, fragrances, buffers, dispersants, conditioning agents such as volatile or non-volatile, modified or unmodified silicones, film-forming agents, ceramides, preserving agents and opacifiers.

27. A process for dyeing keratin fibers, characterized in that the composition comprises the steps of applying the dye composition according to claim 1 to the keratin fibers, and then in leaving it to act for a period of between 3 minutes and 1 hour, and the said fibers are then rinsed.

28. A process for dyeing keratin fibers, characterized in that the composition comprises the steps of applying the dye composition according to claim 1 to the keratin fibers, and then in leaving it to act for a period of between 15 minutes and 45 minutes, and the said fibers are then rinsed.

* * * * *